(12) United States Patent
Chang

(10) Patent No.: US 6,787,524 B2
(45) Date of Patent: Sep. 7, 2004

(54) CPG OLIGONUCLEOTIDES AND RELATED COMPOUNDS FOR ENHANCING ADCC INDUCED BY ANTI-IGE ANTIBODIES

(75) Inventor: Nancy T. Chang, Houston, TX (US)

(73) Assignee: Tanox, Inc., Houston, TX (US)

( * ) Notice: Subject to any disclaimer, the term of this patent is extended or adjusted under 35 U.S.C. 154(b) by 285 days.

(21) Appl. No.: 09/682,562

(22) Filed: Sep. 20, 2001

(65) Prior Publication Data

US 2002/0102255 A1 Aug. 1, 2002

Related U.S. Application Data

(60) Provisional application No. 60/234,881, filed on Sep. 22, 2000.

(51) Int. Cl.[7] .................... A01N 43/04; A01N 61/00; C07K 16/00; C12P 21/08; C07H 21/02
(52) U.S. Cl. ............... 514/44; 435/6; 435/91.1; 435/455; 514/1; 514/2; 530/387.2; 530/387.3; 530/388.1; 530/388.15; 536/23.1
(58) Field of Search ............... 435/6, 7.2, 91.1, 435/455; 530/387.2, 387.3, 388.1, 388.15; 514/44, 1, 2; 536/23.1

(56) References Cited

U.S. PATENT DOCUMENTS

| | | | |
|---|---|---|---|
| 4,171,299 A | 10/1979 | Hamburger | |
| 5,422,258 A | 6/1995 | Chang | |
| 5,428,133 A | 6/1995 | Chang | |
| 5,449,760 A | 9/1995 | Chang | |
| 5,543,144 A | 8/1996 | Chang | |
| 5,614,611 A | * 3/1997 | Chang | 530/387.3 |
| 5,762,943 A | 6/1998 | Dolovich | |
| 5,965,709 A | 10/1999 | Presta et al. | |
| 6,239,116 B1 | 5/2001 | Krieg | |
| 6,538,124 B1 | * 3/2003 | Idusogie et al. | 536/23.53 |
| 6,562,798 B1 | * 5/2003 | Schwartz | 514/44 |
| 6,610,661 B1 | * 8/2003 | Carson et al. | 514/44 |

FOREIGN PATENT DOCUMENTS

| | | |
|---|---|---|
| EP | 0263655 A2 | 4/1988 |
| EP | 0550020 A2 | 7/1993 |
| WO | WO 92/17207 A1 | 10/1992 |
| WO | WO 92/21031 A1 | 11/1992 |
| WO | WO 97/22364 A1 | 6/1997 |
| WO | WO 97/33616 A1 | 9/1997 |
| WO | WO 98/16247 A1 | 4/1998 |
| WO | WO 98/24808 A2 | 6/1998 |
| WO | WO 00/16804 A1 | 3/2000 |
| WO | WO 00/50460 A1 | 8/2000 |

OTHER PUBLICATIONS

Heusser et al., "Therapeutic Potential of anti–IgE Antibodies", Current Opinions in Immunology 9(6):805–813 (1997).
Hook, W.A., et al., "Monoclonal Antibodies Defining Epitopes on Human IgE", Mol. Immunol. 28(6):631–639 (1991).
Spiegelberg, et al., "Inhibition of IgE formation and allergic inflammation by allergen gene immunization and by CpG motif immunostimulatory oligonucleotides" Allergy vol. 53, pp. 93–97 (Sep. 1998).
Voo, K.S. et al., Cloning of a Mammalian Transcriptional Activator That Binds Unmethylated CpG Motifs and Shares a CXXC Domain with DNA Methyltransferase, Human Trithorax, and Methyl–CpG Binding Domain Protein 1, Mol. Cell Biol. 20(6):2108–2121 (2000).
Kreig, A.M., The Role of CpG Motifs in Innate Immunity, Crr. Opin. Immunol. 12:35–43 (2000).
McDonnell, J.M. et al., "Structure based design and characterization of peptides that inhibit IgE binding to its high affinity receptor," Nature Struct. Biol. 3(5):419–426 (1996).
Weigand, T.W. et al., "High Affinity Oligonucleotide Ligands to Human IgE Inhibit Binding to Fcε Receptor I," J. Immunol. 157:221–230 (1996).

* cited by examiner

Primary Examiner—Ram R. Shukla
Assistant Examiner—Jane Zara
(74) Attorney, Agent, or Firm—Cheryl Liljestrand

(57) ABSTRACT

The invention relates to a method of stimulating antibody-dependent cellular cytotoxicity to enhance the elimination of IgE-bearing B-cells comprising administering to a mammal an anti-IgE antibody, which binds to membrane bound IgE, but does not induce histamine release and administering an ISO to the mammal. The ISO may be a CpG containing oligonucleotide, or a modified CpG-containing oligonucleotide with an electron-withdrawing group at least at position C-5 of the cytosine in the CpG sequence. In addition, the method may include the administration of an allergen to improve desensitization therapy.

9 Claims, No Drawings

CPG OLIGONUCLEOTIDES AND RELATED COMPOUNDS FOR ENHANCING ADCC INDUCED BY ANTI-IGE ANTIBODIES

CROSS REFERENCE TO RELATED APPLICATIONS

This application claims priority to U.S. Provisional Application No. 60/234,881 filed Sep. 22, 2000.

FIELD OF THE INVENTION

The present invention provides methods of enhancing the antibody dependent cellular cytotoxicity ("ADCC") effect of anti-IgE to treat IgE-associated disorders.

BACKGROUND OF THE INVENTION

Allergic diseases, including allergic asthma and allergic rhinitis, are characterized by an IgE-mediated early phase response, which occurs within seconds to minutes of allergen exposure, and a late phase response, which is cell-mediated and occurs 4 to 24 hours later. Allergic asthma and allergic rhinitis are characterized by infiltration of eosinophils into the site of allergen exposure. Specifically, during the early phase of the allergic response, activation of Th2-type lymphocytes stimulates the production of antigen-specific IgE antibodies, which are bound by mast-cell and basophil receptors (e.g., Fc $\epsilon$ RI) and which, upon binding an allergen and being cross-linked, in turn trigger the release of histamine and other mediators of inflammation from mast cells and basophils. During the late phase response, IL-4 and IL-5 production by CD4 Th2 cells is elevated. These cytokines appear to play a significant role in recruiting eosinophils into the site of allergen exposure, where tissue damage and lung dysfunction result.

Currently, the standard therapy for many allergic diseases is by desensitization to the allergens. This desensitization involves exposure by injection, over several months, to the allergen, with the expectation that anti-allergen IgG antibodies will be endogenously generated. This therapy has mixed results in patients, and is not effective for many. There is also a risk of anaphylaxis.

A new therapy for treatment of allergic diseases is pending approval by the U.S. FDA and other regulatory agencies. Anti-IgE monoclonal antibodies, which do not bind to IgE bound to the Fc $\epsilon$ RI on basophils or mast cells, can reduce the amount of circulating IgE and provide effective treatment for allergic asthma and allergic rhinitis. See U.S. Pat. Nos. 5,53,144 and 5,614,611. These anti-IgE antibodies may be inducing some level of ADCC and helping to eliminate IgE-producing B cells, which would aid in longer-term suppression of IgE. ADCC is known to be induced by the human Ig isotypes IgG1 and IgG3, as well as by the mouse IgG2a Fc region. Enhancement of ADCC may, therefore, help eliminate IgE-producing B cells and further improve the efficacy of anti-IgE.

Antibody-dependent cellular cytotoxicity or ADCC is the result of Natural Killer (NK) cells recognizing and eliminating a target cell, such as a virally infected cell, coated with IgG antibodies via their Fc $\gamma$ RIII (CD16). The Fc receptor of the NK cell binds to the IgG on the surface of the target cell and mediates ADCC. Macrophages also act as killer cells through ADCC. Specific IgG and IgE molecules enhance the macrophages" ability to kill schistosomules (Roitt, et al., In: Immunology, 5th ed. Mosby, p. 246 (1998)) U.S. Pat. No. 5,500,362 discusses a chimeric IgG monoclonal antibody 2H7, which binds to B-cells and appears to mediate ADCC against lymphoma cells. They suggest its possible usefulness in developing immunoconjugates to deliver drugs, toxins, etc. to tumor cells.

The ADCC events involved in IgE-associated disorders may be enhanced with an immune stimulating nucleotide sequence, including a CpG-containing oligonucleotide, as described in U.S. Pat. No. 6,239,116, as well as related CpG-containing oligonucleotides, and certain related oligonucleotides (hereinafter collectively referred to as "ISOs"). Bacterial CpG-DNA is a potent Th1-like adjuvant triggering a strong Th1 biased antibody response, and concomitantly suppressing the Th2 response (Davis, H. L. et al., *J. Immunol.* 1 60:870–876 (1998)). CpG-DNA is also a potent single B-cell mitogen, which is capable of driving more than 95% of Binto an activated state (Krieg, A. M. et al., *Nature* 374:546–549 (1995)). These innate immune responses can be mimicked by synthesized unmethylated CpG-containing oligodeoxynucleotides (CpG-ODNs). Bactivated by bacterial CpG sequences or CpG-ODNs show increased expression of surface class-II major histocompatibility complex (MHC) molecules and the co-stimulatory molecules B7-1 and B7-2 (Krieg, A. M., In: Delivery Strategies for Antisense Oligonucleotide Therapeutics, Ed. Akhtar, S., CRC Press, Inc., pp 177–190; Davis, H. L. et al., *J. Immunol.* 160: 870–876 (1998)). This suggests the possibility that the CpG "motif," composed of CG dinucleotides, may directly enhance the antigen-presenting function of B-cells. Although the effects of the CpG motif on Tare less clear, highly purified Tthat are stimulated through the T-cell receptor show synergistic proliferative responses to CpGs, indicating a mechanism through which CpGs could promote antigen-specific Tresponses (Bendigs, S. et al., *Eur. J. Immunol.* 29:1209–1218 (1999)).

CpG-ODNs strongly stimulate NK lytic activity and IFN-$\gamma$ production (Tokunaga, T et al., *J. Natl. Cancer Institute* 72:955–962 (1984); Yamamoto S., *J. Immunol.* 148:4072–4076 (1992)). Antigen-presenting cells, such as monocytes and dendritic cells, are activated by CpG-ODNs resulting in the production of Th1 cytokines jakob, T et al., *J. Immunol.* 161:3042–3049 (1998)), as well as MHC-class II molecules and co-stimulatory B7-1 and B7-2 molecules (Stacy, K. J. et al., *J. Immunol.* 1 57:2116–2122 (1996); Sparwasser, T. et al., *Eur. J. Immunol.* 28:2045–2054 (1998)).

CpG-ODNs are, therefore, potent inducers and stimulators of a wide range of antigen-dependent and antigen-independent immune responses. Since CpGactivate NK cells, they are useful for enhancing the antibody dependent cellular cytotoxicity (ADCC) of anti-tumor antibodies. CpGcan shift the Tresponse from a Th2-type response to a Th1-type response, which can result in down-modulating of the allergic responses (Kline, J. N. et al., *J. Immunol.* 160:2555–2559 (1998); Sur, S. et al., *J. Immunol.* 162:5575–5582 (1999); Shirota, H. et al., *J. Immunol.* 164:5575–5582 (2000); Jahn-Schmid, B. et al., *J. Allergy Clin. Immunol.* 104:1015–1023 (1999); Broide, D. H. et al., *J. Clin. Immunol.* 21:175–182 (2001)). Thus, a longer-lasting therapeutic effect in treating IgE-mediated allergic diseases may be achieved by combining desensitization therapy with anti-IgE therapy and an ISO, than with desensitization therapy alone.

DETAILED DESCRIPTION

[Summary]

The present invention provides a method of enhancing the ADCC effect to increase elimination of IgE-bearing B cells to provide a longer-term treatment of IgE-mediated allergic diseases than provided by anti-IgE administration alone. This is achieved by administering an ISO as well as an anti-IgE antibody. Additionally, the invention relates to increasing the effectiveness of desensitization therapy by administering an anti-IgE antibody, an ISO and an allergen (or allergens) to which one is trying to induce desensitization.

In the practice of the invention, the anti-IgE, the ISO and the allergen can be administered to the subject in any order, or simultaneously. Further, the active ingredients described in any of the embodiments herein (i.e., anti-IgE antibody, ISO and allergen) may be combined into a single composition for simultaneous administration of one or more of the active ingredient(s). The ISO can be a CpG-containing oligonucleotide, including those described in U.S. Pat. No. 6,239,116 (incorporated by reference), or an immune stimulatory sequence ("ISS") as described in International Application No. WO 00/16804, or a modified ISS with an electron-withdrawing group at least at position C-5 of the cytosine in the CpG sequence. The electron-withdrawing group can be a bromine, or another such group as described in International Application No. WO 99/62923. The anti-IgE antibody can be E25, E26 or E27, each of which are described in U.S. Pat. No. 5,994,511, or another humanized antibody anti-IgE antibody which does not induce histamine release, including those described in U.S. Pat. No. 5,958,708. Hu-901 is an anti-IgE antibody in development derived from one of the same variable regions as one of the fragments described in U.S. Pat. No. 5,958,708.

All of these anti-IgE antibodies bind to membrane-bound IgE on the surface of IgE-producing B cells. The Th1 response induced by the ISO, which is administered with the anti-IgE antibody or before or after, enhances the ADCC effect of the anti-IgE antibody, and aids in elimination of IgE-producing B cells. A preferred ISO for inducing a Th1 response is described in WO 00/16804. Elimination of IgE-producing B cells results in a decline in the amount of IgE which such cells can produce. The anti-IgE antibody binds free IgE, which is a shorter-term effect. However, the elimination of the IgE-producing B cells by ADCC aids in keeping IgE levels low for extended periods.

If the anti-IgE/ISO administration is also combined with allergen desensitization therapy, as described in WO 00/16804, this may have the added beneficial effect of enhancing the long-term effects of desensitization. The ISO aids in inducing a Th1 response, which enhances the production of anti-allergen IgG, and which further aids in reducing the circulating free IgE for extended periods.

The allergen can be administered as a free allergen, or conjugated to the ISO, as described in WO 00/16804. The conjugated allergen-ISO may be preferred, and result in greater therapeutic efficacy than an unconjugated allergen and an ISO.

Antibody molecules of the present invention include polyclonal or monoclonal antibodies, single chain antibodies, as well as functional fragments thereof. Monoclonal antibodies include chimeric or humanized antibodies, human antibodies, or DeImmunised™ antibodies. Fragments of these antibodies include Fv, Fab, F(ab")$_2$, single or double chain Fv fragments which retain the antigen binding function of the parent antibody. The antibody may be produced by any recombinant method known in the art and may be produced in vitro or in vivo. Single chain antibodies ("ScFv") and the method of their construction are described in U.S. Pat. No. 4,946,778.

Techniques for producing antibodies follow:
[Monoclonal Antibodies]

Monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these myeloma cell lines are murine myeloma lines, such as those derived from MOPC-21 and MPC-11 mouse tumors available from the Salk Institute Cell Distribution Center, San Diego, Calif. USA, and SP2/0 or X63-Ag8–653 cells available from the American Type Culture Collection, Rockville, Md. USA. Human myeloma and mouse-human heteromyeloma cell lines also have been described for the production of human monoclonal antibodies (Kozbor, J. Immunol. 133:3001 (1984); Brodeur et al., Monoclonal Antibody Production Techniques and Applications, pp. 51–63 (Marcel Dekker, Inc., New York, 1987)). The mouse myeloma cell line NSO may also be used (European Collection of Cell Cultures, Salisbury, Wiltshire UK).

Culture medium in which hybridoma cells are grown is assayed for production of monoclonal antibodies directed against the antigen. The binding specificity of monoclonal antibodies produced by hybridoma cells may be determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp.59–103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (Innis M. et al. In PCR Protocols. A Guide to Methods and Applications, Academic, San Diego, Calif. (1990), Sanger, F. S, et al. *Proc. Nat. Acad. Sci.* 74:5463–5467 (1977)). The hybridoma cells serve as a source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., *Nature* 348:552–554 (1990). Clackson et al., *Nature* 352:624–628 (1991) and Marks et al., *J. Mol. Biol.* 222:581–597 (1991) describe the isolation of murine and human antibodies, respectively, using phage libraries. Subsequent publications describe the production of high affinity (nM range) human antibodies by chain shuffling (Marks et al., *Bio/Technology* 10:779–783 (1992)), as well as combinatorial infection and in vivo recombination as a strategy for constructing very large phage libraries (Waterhouse et al., *Nuc. Acids. Res.* 21:2265–2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Nat. Acad. Sci.* USA 81:6851 (1984)), or by covalently joining to the immunoglobulin coding sequence all or part of the coding sequence for a non-immunoglobulin polypeptide.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Another alternative is to use electrical fusion rather than chemical fusion to form hybridomas. This technique is well established. Instead of fusion, one can also transform a B-cell to make it immortal using, for example, an Epstein Barr Virus, or a transforming gene. (See, e.g., "Continuously Proliferating Human Cell Lines Synthesizing Antibody of Predetermined Specificity," Zurawaki, V. R. et al, in Monoclonal Antibodies, ed. by Kennett R. H. et al, Plenum Press, N.Y. 1980, pp 19–33.)

[Humanized and Human Antibodies]

A humanized antibody has one or more amino acid residues introduced into it from a source, which is non-human. These non-human amino acid residues are often referred to as "import" residues, which are typically taken from an "import" variable domain. Humanization can be essentially performed following the method of Winter and co-workers (Jones et al., *Nature* 321:522–525 (1986); Riechmann et al., *Nature* 332:323–327 (1988); Verhoeyen, et al., *Science*, 239:1534–1536 (1988)), by substituting rodent CDRs or CDR sequences for the corresponding sequences of a human antibody. Accordingly, such "humanized" antibodies have substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci.* USA, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, the skilled researcher can produce transgenic animals (e.g., mice) that are capable, upon immunization, of producing a full repertoire of human antibodies in the absence of endogenous immunoglobulin production. Such transgenic mice are available from Abgenix, Inc., Fremont, Calif., and Medarex, Inc., Annandale, N.J. It has been described that the homozygous deletion of the antibody heavy-chain joining region OH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc Natl. Acad. Sci.* USA 90:2551 (1993); Jakobovits et al., *Nature* 362:255–258 (1993); Bruggermann et al., *Year in Immunol.* 7:33 (1993); and Duchosal et al. *Nature* 355:258 (1992). Human antibodies can also be derived from phage-display libraries (Hoogenboom et al., *J. Mol. Biol.* 227:381 (1991); Marks et al., *J. Mol. Biol.* 222:581–597 (1991); Vaughan, et al., *Nature Biotech* 14:309 (1996)).

[DeImmunized Antibodies]

DeImmunised™ antibodies are antibodies in which the potentialT cell epitopes have been eliminated, as described in International Patent Application PCT/GB98/01473. Therefore, immunogenicity in humansis expected to be eliminated or substantially reduced when they are applied in vivo. Additionally, antibodies can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546 which are all hereby incorporated by reference in their entireties. Preferred polymers are polyoxyethylated polyols and polyethylene glycol (PEG). PEG is soluble in water at room temperature and has a preferred average molecular weight between 1000 and 40,000, more preferably between 2000 and 20,000, most preferably between 3,000 and 12,000.

[Administration]

Pharmaceutical vehicles may be used to control the duration of action of the molecules of the invention. They could be entrapped in microcapsules prepared by coacervation techniques or by interfacial polymerization (hydroxymethylcellulose or gelatin microcapsules) in colloidal drug delivery systems (for example, liposomes, albumin microspheres, microemulsions, nano-particles and nanocapsules) or in macroemulsions. Methods of preparing liposome delivery systems are discussed in Gabizon et al., *Cancer Research* 42:4734 (1982); Cafiso, *Biochem Biophys Acta* 649:129(1981); and Szoka, *Ann RevBiophys Eng* 9:467 (1980). Other drug delivery systems are known in the art and are described in, e.g., Poznansky et al., In: Drug Delivery Systems (R. L. Juliano, ed., Oxford, N.Y. 1980), pp. 253–31 5; M. L. Poznansky, *Pharm Revs* 36:277 (1984).

Liquid pharmaceutical compositions may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example), which may include additional ingredients. Upon reconstitution, the composition is administered to subjects.

The molecules of the present invention can be administered by any of a number of routes and are administered at a concentration that is therapeutically effective in the indication or for the purpose sought. To accomplish this goal, the antibodies may be formulated using a variety of acceptable excipients known in the art. Typically, the antibodies are administered by injection, either intravenously or intraperitoneally. Methods to accomplish this administration are known to those of ordinary skill in the art. It may also be possible to obtain compositions which may be topically or orally administered, or which may be capable of transmission across mucous membranes.

The dosage and mode of administration will depend on the individual and the agent to be administered. The dosage can be determined by routine experimentation in clinical trials or extrapolation from animal models in which the antibody was effective. Dosage and protocols for administering allergen for immunotherapy depend on the allergen to be administered and the individual being treated, but known to the skilled practitioner. Generally, the allergen may be administered on a weekly basis and in a higher does than would be possible in the absence of anti-IgE. The amount of allergen to be administered is an amount sufficient to induce desensitization to the allergen, as long as the dose is below that which would cause anaphylaxis. Concentrations of allergens are known in the art. Examples of commonly administered allergens include, e.g., bee, dust mite, shrimp, cat, dog, mollusks, various nuts, such as peanut or walnut, ragweed, various molds/fungi, various tree allergens, etc.

The amount of ISO to be administered would be in an amount sufficient to enhance ADCC and anti-IgE activity. As one skilled in the art would recognize, this enhancement of ADCC may be identified using standard methods in the art, such as measuring the amount of cytokines produced indicative of a Th1 response.

The foregoing description, terms, expressions, and examples are exemplary only and not limiting. The invention includes all equivalents of the foregoing embodiments, both known and unknown. The invention is limited only by the claims that follow and not by any statement in any other portion of this document or in any other source.

What is claimed is:

1. A method of stimulating antibody dependent cellular cytotoxicity ("ADCC") to enhance the elimination of IgE-bearing B cells comprising:
    administering to a mammal an anti-IgE antibody which binds to membrane bound IgE, but does not induce histamine release; and
    administering an immune stimulatory oligonucleotide ("ISO") to the mammal.

2. The method of claim 1 wherein the ISO is a CpG containing oligonucleotide, or a modified CpG-containing oligonucleotide with an electron-withdrawing group at position C-5 of the cytosine in the CpG sequence.

3. The method of claim 1 wherein the antibody has a human IgG1 or IgG3 Fc portion, or a mouse IgG2a Fc region.

4. The method of claim 2 wherein the anti-IgE antibody is Hu-901, E25, E26 or E27.

5. The method of any of claims 1 to 4, further including administering an allergen to the mammal.

6. The method of claim 5 wherein the allergen is conjugated to the CpG-containing oligonucleotide.

7. The method of claim 5 wherein the mammal is a human being.

8. The method of claim 5 wherein the CpG-containing oligonucleotide has the formula: NDCGHN (SEQ ID NO 5), wherein N is any nucleotide, D is any nucleotide other than cytosine and H is any nucleotide other than guanine.

9. The method of claim 5 wherein CpG-containing oligonucleotide has one of the following sequences: AACGTTCC (SEQ ID NO 1), AACGTCG (SEQ ID NO 2), GACGTTCC (SEQ ID NO 3) or GACGTTCG (SEQ ID NO 4).

* * * * *

SEQUENCE LISTING

<160> NUMBER OF SEQ ID NOS: 5

<210> SEQ ID NO 1
<211> LENGTH: 8
<212> TYPE: DNA
<213> ORGANISM: Artificial Sequence
<220> FEATURE:
<223> OTHER INFORMATION: CpG containing oligonucleotide

<400> SEQUENCE: 1 aacgttcc                                                                 8

<210> SEQ ID NO 2
<211> LENGTH: 7
<212> TYPE: DNA
<213> ORGANISM: Artificial Sequence
<220> FEATURE:
<223> OTHER INFORMATION: CpG containing oligonucleotide

<400> SEQUENCE: 2 aacgtcg                                                                  7

<210> SEQ ID NO 3
<211> LENGTH: 8
<212> TYPE: DNA

-continued

```
<213> ORGANISM: Artificial Sequence
<220> FEATURE:
<223> OTHER INFORMATION: CpG containing oligonucleotide

<400> SEQUENCE: 3 gacgttcc                                                                   8

<210> SEQ ID NO 4
<211> LENGTH: 8
<212> TYPE: DNA
<213> ORGANISM: Artificial Sequence
<220> FEATURE:
<223> OTHER INFORMATION: CpG containing oligonucleotide

<400> SEQUENCE: 4 gacgttcg                                                                   8

<210> SEQ ID NO 5
<211> LENGTH: 6
<212> TYPE: DNA
<213> ORGANISM: Artificial Sequence
<220> FEATURE:
<223> OTHER INFORMATION: CpG containing oligonucleotide
<221> NAME/KEY: misc_feature
<223> OTHER INFORMATION: N is any nucleotide

<400> SEQUENCE: 5 ndcghn                                                                     6
```